United States Patent [19]

Schade et al.

[11] Patent Number: 4,855,318
[45] Date of Patent: Aug. 8, 1989

[54] IODOPROPARGYL ETHERS USEFUL AS ANTIMICROBIAL AGENTS

[75] Inventors: Gerold Schade, Cologne; Wilfried Paulus, Krefeld; Hans-Georg Schmitt, Leverkusen, all of Fed. Rep. of Germany

[73] Assignee: Bayer Aktiengesellschaft, Leverkusen, Fed. Rep. of Germany

[21] Appl. No.: 67,674

[22] Filed: Jun. 26, 1987

Related U.S. Application Data

[62] Division of Ser. No. 834,287, Feb. 27, 1986, Pat. No. 4,719,227.

[30] Foreign Application Priority Data

Mar. 21, 1985 [DE] Fed. Rep. of Germany ....... 3510203

[51] Int. Cl.$^4$ ................ A01N 43/08; C07D 317/16; C07D 317/34; C07D 307/12
[52] U.S. Cl. .................................. 514/467; 514/462; 514/461; 514/473; 549/453; 549/455; 549/497; 549/475; 549/341; 549/331
[58] Field of Search ............... 549/347, 374, 372, 423, 549/453, 427, 558, 554, 497, 341, 331, 475, 455; 514/462, 467, 473, 461

[56] References Cited

U.S. PATENT DOCUMENTS 3,290,388 12/1966 Burger et al. ................. 549/374
3,700,698 10/1972 Beaman et al. ............... 549/558
4,338,327 7/1982 Heeres et al. ................. 514/383

FOREIGN PATENT DOCUMENTS 3304899 8/1984 Fed. Rep. of Germany .

OTHER PUBLICATIONS

Chemical Abstracts, Band 101, No. 19, 5 Nov. 1984, Seite 706, Zusammenfassung No. 171277d, Columbus, Ohio, US; & CS-A-211 195 (D. Hesoun et al.) 15-0-2-1984 *Zusammenfassung*.

J. Org. Chem., Band 47, No. 4, 12 Jan. 1982, Seiten 725-730, American Chemical Society, US; R. J. Sundberg et al.: "Synthesis and Intramolecular cycloaddition reactions of some 3-substituted 6-azidohexa-2,4-dienoate esters", *Seite 729, Verbindunger 1,2*.

Primary Examiner—Nicky Chan
Attorney, Agent, or Firm—Sprung Horn Kramer & Woods

[57] ABSTRACT

Iodopropargyl ethers of the formula

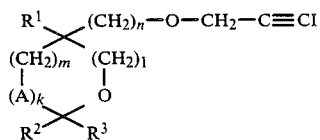

wherein
A represents oxygen or a methylene group,
$R^1$ denotes hydrogen or lower alkyl,
$R^2$ and $R^3$ are identical or different and represent hydrogen, lower alkyl, alkenyl or unsubstituted or halogen-substituted phenyl, or $R^2$ and $R^3$ together form a carbocyclic ring with 4 to 7 C atoms,
l and m represent 0, 1 or 2,
k denotes 0 or 1 and
n denotes an integer from 0 to 4, with the proviso that if l is 0, n represents 1, 2, 3 or 4, can be prepared by reaction of the corresponding propargyl ethers with iodinating agents. The iodopropargyl ethers are active compounds in microbicidal agents.

16 Claims, No Drawings

IODOPROPARGYL ETHERS USEFUL AS ANTIMICROBIAL AGENTS

This is a division, of application Ser. No. 834,287, filed Feb. 27, 1986, now U.S. Pat. No. 4,719,227.

BACKGROUND OF THE INVENTION

The invention relates to new iodopropargyl ethers, a process for their preparation and their use in microbicidal agents.

It is known from DE-OS (German Published Specification) No. 3,304,899 that iodopropargyl ethers, such as 1-(3-iodo-2-propinyloxy)-propane-2,3-diol, can be used as antimicrobial substances. Their not always satisfactory acitivity is a disadvantage.

SUMMARY OF THE INVENTION

New iodopropargyl ethers of the formula

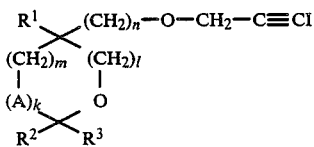

wherein

A represents oxygen or a methylene group, $R^1$ denotes hydrogen or lower alkyl, $R^2$ and $R^3$ are identical or different and represent hydrogen, lower alkyl, alkenyl or unsubstituted or halogen-substituted phenyl, or $R^2$ and $R^3$ together form a carbocyclic ring with 4 to 7 carbon atoms, l and m represent 0, 1 or 2, k denotes 0 or 1, and n denotes an integer from 0 to 4, with the proviso that if l is 0, n represents 1, 2, 3 or 4 have been found.

According to the invention, lower alkyl in general denotes a straight-chain or branched hydrocarbon radical with 1 to 6 carbon atoms, preferably 1 to 4 carbon atoms. Radicals which may be mentioned specifically are: methyl, ethyl, propyl, isopropyl, butyl, isobutyl, pentyl, isopentyl, hexyl and isohexyl. The methyl and the ethyl radical are preferred.

According to the invention, halogen denotes fluorine, chlorine, bromine and iodine, preferably chlorine.

If $R^2$ and $R^3$ together form a carbocyclic ring, a carbocyclic ring with 5 to 6 carbon atoms is preferred.

Preferred new iodopropargyl ethers are those of the formula

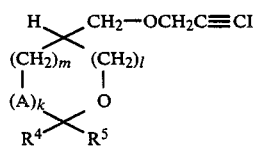

wherein

A represents oxygen or a methylene group, $R^4$ denotes hydrogen or lower alkyl, $R^5$ represents hydrogen, lower alkyl, phenyl or chlorophenyl, l and m represent 0, 1 or 2 and k denotes 0 or 1.

The following new iodopropargyl ethers may be mentioned as examples: 2-(4-chlorophenyl)-5-iodopropargyloxy-1,3-dioxane, 2,2-dimethyl-4-(4-iodopropargyloxybutyl)-1,3-dioxolane, 5-ethyl-5-iodopropargyloxymethyl-1,3-dioxane, 2,2-dimethyl-5-ethyl-5-iodopropargyloxymethyl-1,3-dioxane, 2,2,5-trimethyl-5-iodopropargyloxymethyl-1,3-dioxane, 3-iodopropargyloxy-tetrahydrofuran, 3-methyl-3-iodopropargyloxymethyl-oxetane, 3-ethyl-3-iodopropargyloxymethyl-oxetane, 4-iodopropargyloxymethyl-1,3-dioxolane, 2-methyl-4-(iodopropargyloxymethyl)-1,3-dioxolane, 2,2-dimethyl-4-(iodopropargyloxymethyl)-1,3-dioxolane, 2-methyl-2-ethyl-4-(iodopropargyloxymethyl)-1,3-dioxolane, 2,2-pentamethylene-4-(iodopropargyloxymethyl)-1,3-dioxolane, 2-phenyl-4-(iodopropargyloxymethyl)-1,3-dioxolane, 2-iodopropargyloxymethyl-tetrahydrofuran, 2-iodopropargyloxymethyl-tetrahydropyran and 2-methyl-2-phenyl-4-(iodopropargyloxymethyl)-1,3-dioxolane, preferably 4-(iodopropargyloxymethyl-1,3-dioxolane, 2-methyl-4-(iodopropargyloxymethyl)-1,3-dioxolane, 2,2-dimethyl-4-(iodopropargyloxymethyl)-1,3-dioxolane, 2-methyl-2-ethyl-4-(iodopropargyloxymethyl)-1,3-dioxolane, 2,2-pentamethylene-4-(iodopropargyloxymethyl)-1,3-dioxolane, 2-phenyl-4-(iodopropargyloxymethyl)-1,3-dioxolane, 2-iodopropargyloxymethyl-tetrahydrofuran, 2-iodopropargyloxymethyl-tetrahydropyran and 2-methyl-2-phenyl-4-(iodopropargyloxymethyl)-1,3-dioxolane.

A process has furthermore been found for the preparation of the new iodopropargyl ethers of the formula

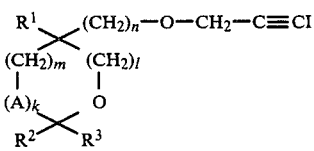

wherein

A represents oxygen or a methylene group, $R^1$ denotes hydrogen or lower alkyl, $R^2$ and $R^3$ are identical or different and represent hydrogen, lower alkyl, alkenyl or unsubstituted or halogen-substituted phenyl, or together form a carbocyclic ring with 4 to 7 carbon atoms, l and m represent 0, 1 or 2, k denotes 0 or 1, and n denotes an integer from 0 to 4, with the proviso that if l is 0, n represents 1, 2, 3 or 4 characterized in that propargyl ethers of the formula

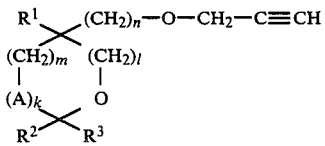

wherein

A, $R^1$, $R^2$, $R^3$, l, m, n and k have the abovementioned meaning, are reacted with iodinating agents in the presence of solvents and/or diluents and in the presence of bases at temperatures of $-10°$ to $30°$ C.

DETAILED DESCRIPTION OF THE INVENTION

Iodinating agents which can be employed in the process according to the invention are iodine and/or compounds which supply iodide ions, such as sodium iodide and ammonium iodide, in the presence of oxidizing agents, such as sodium hypochlorite, calcium hypochlorite and hydrogen peroxide.

Suitable bases for the process according to the invention include both inorganic and organic bases, such as sodium hydroxide, calcium hydroxide, sodium methylate, potassium tert.-butylate and sodium isobutylate, preferably sodium hydroxide and sodium methylate.

Examples of suitable solvents for the process according to the invention are water or alcohols, such as methanol and/or ethanol, or mixtures thereof.

The iodination is preferably carried out at temperatures from $-5°$ to $+20°$ C.

According to the inventionn, 1 mole of propargyl ether of the general formula (III) is reacted with about 1 to 1.5 moles of iodinating agent, preferably 1 to 1.2 moles of iodinating agent.

The most favorable amounts of bases and solvents and/or diluents in each case can easily be determined by preliminary experiments. About 1 to 3, preferably 1.5 to 2, moles of base per mole of propargyl ether of the general formula (III) and the same to five times, preferably twice to three times, the amount by weight of solvent and/or diluent are usually employed.

The propargyl ethers of the general formula (III) to be employed for the preparation of the new iodopropargyl ethers of the formula (I) are known in some cases (compare U.S. Pat. No. 3,290,388). They can be prepared by a process analogous to those described therein, in which the corresponding hydroxy compounds of the general formula $$\begin{array}{c} R^1 \diagdown \diagup (CH_2)_n\text{—}OH \\ (CH_2)_m \quad (CH_2)_l \\ | \qquad | \qquad \xrightarrow{\text{1. Base}}_{\text{2. }X\text{—}CH_2\text{—}C\equiv CH} (IV) \\ (A)_k \quad O \\ R^2 \diagup \diagdown R^3 \end{array}$$

wherein
A represents oxygen or a methylene group,
$R^1$ denotes hydrogen or lower alkyl,
$R^2$ and $R^3$ are identical or different and represent hydrogen, lower alkyl, alkenyl or unsubstituted or halogen-substituted phenyl, or together form a carbocyclic ring with 4 to 7 carbon atoms,
l and m represent 0, 1 or 2,
k denotes 0 or 1, and
n denotes an integer from 0 to 4, with the proviso that is l is 0, n represents 1, 2, 3 or 4.
are reacted with propargyl halides in the presence of bases and in the presence of solvents and/or diluents at temperatures from about 0° to 100° C.

Strong bases, such as sodium hydride, sodium amide and/or potassium tert.-butylate, are particularly suitable bases for the reaction.

Propargyl halides which may be utilized are propargyl chloride and propargyl bromide, preferably propargyl chloride.

Solvents which can be employed are those solvents which are inert towards the bases used; examples of possible solvents are dimethylformamide, tetrahydrofuran, dimethoxyethane and/or toluene.

The reaction of the hydroxy compounds of the formula (IV) is advantageously carried out by a procedure in which the deprotonation with the base is first carried out, and in particular such that low reaction temperatures are initially used (about 0° to 20° C.) and the reactions are then brought to completion by warming to temperatures from about 20° to 60° C.

After the deprotonation has taken place, the corresponding propargyl halide is added. The reaction temperature required to form the ether in general depends on the reactivity of the alcoholate of the compound (IV) and is in general about 20° to 100° C., preferably 20° to 60° C. If it should be necessary, the temperature can be increased further during the reaction.

It may furthermore be advantageous to carry out the reaction of the hydroxy compound of the formula (IV) with a base and a propargyl halide in an aqueous-organic two-phase system under phase transfer catalysis. It is then possible to employ sodium hydroxide as the base. Examples of suitable organic solvents for the phase transfer reaction are methylene chloride, tetrahydrofuran and/or toluene. Phase transfer catalysts which can be employed are the known tetraalkylammonium salts, such as triethylbenzylammonium chloride, tetrabutylammonium bromide and dimethyldodecylbenzylammonium chloride, or crown ethers, such as 18-crown-6 and dibenzo-18-crown-6 (compare Dehmlow and Dehmlow, Phase Transfer Catalysis, Weinheim 1983).

The amount of bases, hydroxy compounds of the formula (IV) and propargyl halides to be employed can in turn be easily determined by preliminary experiments.

Some of the hydroxy compounds of the general formula (IV) are known from the literature. If A is oxygen and k is 1, they can be prepared by a process analogous to that described in *Organic Syntheses Coll.*, Vol. 3, page 502, in which trihydroxy compounds of the formula $$\begin{array}{c} R^1 \diagdown \diagup (CH_2)_n\text{—}OH \\ (CH_2)_m \quad (CH_2)_l \\ | \qquad \quad | \\ OH \qquad \quad OH \end{array} \qquad (V)$$

wherein
$R^1$, l, m and n have the abovementioned meaning,
are subjected to a condensation reaction with carbonyl compounds of the formula $$R^2\text{—}CO\text{—}R^3 \qquad (VI)$$

wherein
$R^2$ and $R^3$ have the abovementioned meaning,
water being split off.

If, for example, glycerol is reacted with carbonyl compounds, depending on the nature of the carbonyl compound, dioxolanes (VII) or dioxanes (VIII) can be formed (see the following equation).

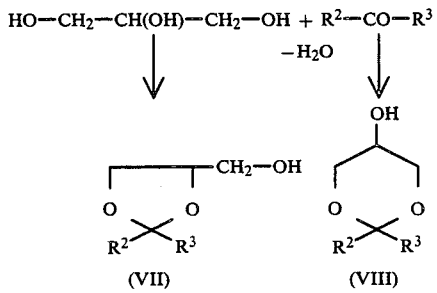

In this reaction, mixtures from which the pure compounds (VII) and (VIII) can be isolated by known separation methods, for example, distillation or chromatography, are occasionally obtained. It may also be advantageous to employ the mixture in the subsequent synthesis steps, in which case a mixture of new iodopropargyl ethers according to the invention is finally obtained.

The iodopropargyl ethers of the formula

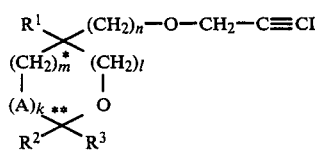

according to the invention can form stereoisomers. Thus, the carbon atom labelled with an asterisk is chiral if l differs from m or A is other than oxygen. If $R^2$ additionally differs from $R^3$ in these cases, the carbon atom labelled with two asterisks is also chiral. However, even if the carbon atoms labelled are not chiral, cis/trans-isomers in respect of the ring system can be formed; that is to say when $R^2$ differs from $R^3$.

The possible enantiomers, diastereomers and cis-/trans-isomers of the iodopropargyl ethers according to the invention can be separated by known methods, for example by crystallisation, distillation or reaction with chiral auxiliary reagents (compare E. Eliel, *Stereochemie der Kohlenstoffverbindungen* (Stereochemistry of Carbon Compounds), Weinheim 1966).

However, it may frequently be advantageous to dispense with the separation and to use the isomer mixtures.

The invention comprises both the pure isomers and mixtures thereof.

The new iodopropargyl ethers according to the invention can be used as active compounds for combating microorganisms, in particular for the preservation of industrial materials.

According to the invention, industrial materials are non-living materials which have been prepared for use in industry. For example, industrial materials which are to be preserved, by active compounds according to the invention, from microbial change or destruction can be adhesives, sizes, paper and card, textiles, leather, wood, paints and articles made of plastic, cooling lubricants and other materials which can be attacked or decomposed by microorganisms. Components of production plants, for example cooling water circulations, which can be impaired by multiplication of microorganisms, may also be mentioned in the context of the materials to be preserved. Preferred industrial materials which may be mentioned in the context of the present invention are adhesives, sizes, paper and card, leather, wood, paints, cooling lubricants and cooling circulations.

Examples which may be mentioned of microorganisms which can effect degradation or a change in the industrial materials are bacteria, fungi, yeasts, algae and slime organisms. The active compounds according to the invention preferentially act against fungi, in particular mold fungi, fungi which discolor and destroy wood (Basidiomycetes), and against slime organisms and algae.

Microorganisms of the following genera may be mentioned as examples: Alternaria, such as *Alternaria tenuis*, Aspergillus, such as *Aspergillus niger*, Chaetomium, such as *Chaetomium globosum*, Coniophora, such as *Coniophora puteana*, Lentinus, such as *Lentinus tigrinus*, Penicillium, such as *Penicillium glaucum*, Polyporus, such as *Polyporus versicolor*, Aureobasidium, such as *Aureobasidium pullulans*, Sclerophoma, such as *Sclerophoma pityophila*, Trichoderma, such as *Trichoderma viride*, Escherichia, such as *Escherichia coli*, Pseudomonas, such as *Pseudomonas aeroginosa* and Staphylococcus, such as *Staphylococcus aureus*.

Depending on the field of application, an active compound according to the invention can be converted into the customary formulations, such as solutions, emulsions, suspensions, powders, pastes and granules.

These can be prepared in a manner which is known per se, for example by mixing the active compounds with an extender, which consists of a liquid solvent and/or solid carriers, if appropriate using surface-active agents, such as emulsifiers and/or dispersing agents, and, if appropriate, in the case of the use of water as the extender, organic solvents, such as alcohols, can be used as auxiliaries.

Liquid solvents for the active compound can be, for example, water, alcohols, such as lower aliphatic alcohols, preferably ethanol or isopropanol, or benzyl alcohol, ketones, such as acetone or methyl ethyl ketone, liquid hydrocarbons, such as benzine fractions, and halogenated hydrocarbons, such as 1,2-dichloroethane.

Microbicidal agents in general contain the active compounds in an amount of 1 to 95%, preferably 10 to 75%.

The use concentrations of the active compounds according to the invention depend on the nature and the ocurrence of the microorganisms to be combated, and on the composition of the material to be preserved. The optimum amount to be employed can be determined by means of series of tests. The use concentrations are in general in the range from 0.001 to 5% by weight, preferably from 0.05 to 1.0% by weight, relative to the material to be preserved.

The active compounds according to the invention can also be in a mixture with other known active compounds. The following active compounds may be mentioned as examples: benzyl alcohol mono(poly)hemiformal and other compounds which split off formaldehyde, benzimidazolyl methylcarbamates, tetramethylthiuram disulphide, zinc salts of dialkyldithiocarbamates, 2,4,5,6-tetrachloroisophthalonitrile, thiazolylbenzimidazole, mercaptobenzothiazole, organo-tin compounds, methylenebisthiocyanate and phenol derivatives, such as 2-phenylphenol, (2,2'-dihydroxy-5,5'-dichloro)diphenylmethane and 3-methyl-4-chlorophenol.

PREPARATION EXAMPLES (A) Preparation of dioxolanes and dioxanes 1 mole of the corresponding trihydroxy compound, 1 to 4 moles of the corresponding carbonyl compound, 300 ml of petroleum ether and 3 g of p-toluenesulphonic acid were heated, using a water separator, until the formation of water had ended. 3 g of sodium acetate were added, the mixture was stirred for 30 minutes and filtered, the filtrate was concentrated and the residue was distilled.

The following compounds were thus obtained:

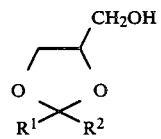

| Example No. | $R^1$ | $R^2$ | Boiling point (°C.)/pressure (mbar) | Yield | Remarks |
|---|---|---|---|---|---|
| 1 | $CH_3$ | $CH_3$ | 80/20 | 84% | |
| 2 | $CH_3$ | $C_2H_5$ | 93/20 | 81% | |
| 3 | —$(CH_2)_5$— | | 97/0.4 | 71% | |
| 4 | $C_6H_5$ | $CH_3$ | 140/1.5 | 81% | |
| 5 | 4-Cl—$C_6H_4$ | $CH_3$ | 150/0.9 | 34% | |
| 6 | H | $CH_3$ | 64/2.5 | 53% | x |
| 7 | H | $C_6H_5$ | 120/1.2 | 62% | x |
| 8 | H | 4-Cl—$CH_4$ | Melting point 110° C. | 23% | x |

| Example No. | | Boiling point/pressure | Yield |
|---|---|---|---|
| 9 | (CH₂)₄OH structure with CH₃, CH₃ | 121/20 | 45% |
| 10 | R, CH₂OH structure  R = $CH_3$ | 110/8 | 84% |
| 11 | R = $C_2H_5$ | 112/0.35 | 76% | x Mixture with the corresponding dioxane

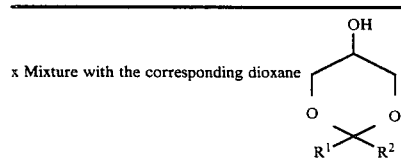

(B) Preparation of propargyl ethers (a) 1.05 moles of sodium hydride were suspended in dimethylformamide and 1 mole of hydroxy compound was added dropwise. The mixture was subsequently stirred until the evolution of hydrogen had ended. 1.1 moles of chloropropine were then added dropwise and the mixture was subsequently stirrred until the reaction had proceeded to completion. The mixture was filtered, the filtrate was concentrated and the residue was distilled.

The following compounds were thus obtained:

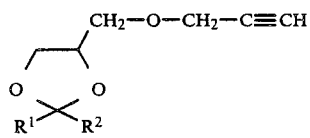

| Example No. | $R^1$ | $R^2$ | Boiling point/Pressure | Yield | Remarks |
|---|---|---|---|---|---|
| 12 | $CH_3$ | $CH_3$ | 83/3,3 | 44% | |
| 13 | $CH_3$ | $C_2H_5$ | 67/0,7 | 55% | |
| 14 | —$(CH_2)_5$— | | 103/1,2 | 70% | |
| 15 | $C_6H_5$ | $CH_3$ | 120/1,5 | 25% | |
| 16 | 4-Cl—$C_6H_4$ | $CH_3$ | 132/0,6 | 35% | |
| 17 | H | $CH_3$ | 40-60/1,0 | 43% | x |
| 18 | H | $C_6H_5$ | 119/0,8 | 29% | x |
| 19 | 4-Cl—$C_6H_4$ derivative with O—$CH_2$—C≡CH | | Melting Point 102° C. | 44% | |

| Example No. | | Boiling point/pressure | Yield |
|---|---|---|---|
| 20 | $(CH_2)_4O$—$CH_2$—C≡CH with $CH_3$, $CH_3$ | 93/0,6 | 61% |
| 21 | R, $CH_2$—O—$CH_2$—C≡CH, R = $CH_3$ | 85/2 | 47% |
| 22 | R = $C_2H_5$ | 82/1 | 38% |
| 23 | $(CH_2)_k$ cyclic structure, k = 0 | 57/0,5 | 16% |
| 24 | k = 1 | 70/4 | 34% |
| 25 | tetrahydrofuran O—$CH_2$—C≡CH | 74/18 | 21% |

| | | | |
|---|---|---|---|
| 26 |  C₂H₅, CH₂—O—CH₂—C≡CH | 92/3,5 | 17% | x mixture with the corresponding dioxane

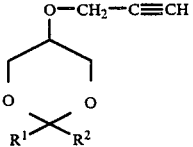

(b) 0.5 mole of hydroxy compound, 0.55 mole of chloropropine, 0.025 mole of tetrabutylammonium bromide, 150 ml of toluene and 250 ml of 50% strength NaOH were stirred first at 20° C. for 1 hour and then at 60° C. for 1.5 hours. The organic phase was separated off and concentrated. The residue could be employed in the iodination without further purification.

The following compounds were thus obtained:

| Example | Structure | Yield |
|---|---|---|
| 26 a |  CH₂OCH₂C≡CH | 83% |
| 26 b | C₂H₂, CH₂OCH₂≡CH 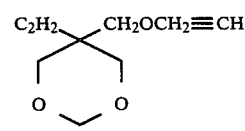 | 85% |
| 26 c | CH₃, CH₂OCH₂C≡CH 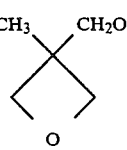 | 56% |

(C) Preparation of iodopropargyl ethers 1 mole of propargyl ether was dissolved in methanol and the solution was cooled to 0° C. 1.5 moles of aqueous sodium hydroxide solution and 1.1 moles of iodine were added and the mixture was subsequently stirred at 0° to 5° C. When the iodination had ended, the reaction mixture was concentrated, water was added, the mixture was decolorised with sodium thiosulphate and taken up in methylene chloride and the resulting mixture was concentrated. The products were in general isolated as an oil, and in some cases crystallisation occurred.

The following compounds were thus obtained:

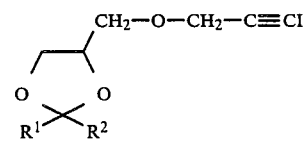

| Example No. | R¹ | R² | ¹H—NMR, δ = | Yield | Remarks |
|---|---|---|---|---|---|
| 27 | CH₃ | CH₃ | 1.35(s, 3H); 1.42(s, 3H); 3.5–4.3 (m, 5H);4.35(s, 2H); | 91% | |
| 28 | CH₃ | C₂H₅ | 0.9(m, 3H); 1.29/1.34(2s, 3H); 1.7 (m, 2H); 3.5–4.3(m, 5H); 4.33(s, 2H); | 86% | cis/trans |
| 29 | —(CH₂)₅— | | 1.2–1.8(m, 10H); 3.5–4.3(m, 5H); 4.32(s, 2H); | 80% | |
| 30 | C₆H₅ | CH₃ | 1.64/1.67(2s, 3H); 3.3–4.2(m, 5H); 4.25/4.37(2s, 2H); 7.2–7.5(m, 5H); | 99% | cis/trans |
| 31 | 4-Cl—C₆H₄ | CH₃ | 1.60/1.64(2s, 3H); 3.3–4.2(m, 5H); 4.25/4.37(2s, 2H); 7.2–7.4(m, 4H); | 100% | cis/trans |
| 32 | H | CH₃ | 1.3–1.4(m, 3H); 3.5–4.4(m, 5H); 4.34–4.46(2s, 2H); 4.55/4.70/5.00/ 5.10(4q, 1H) | 86% | x |
| 33 | H | C₆H₅ | 3.6–4.5(m, 5H); 4.35/4.38(2s, 2H); 5.53/5.80/5.93 (4s, 1H); | 99% | x |
| 33a | H | H | 3.3–4.3(m, 5H); 4.34/4.37(2s, 2H); 4.70/4.84 (AB); 4.86/5.00 (AB) (together 2H) | 46% | x |

| Example No. | | ¹H—NMR δ = | Yield |
|---|---|---|---|
| 34 | 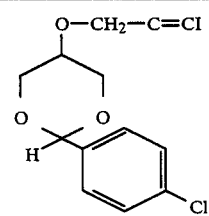 | 3.58(s, 1H); 4.03/4.30 (AB, 4H); 4.45(s, 2H); 5.46(s, 1H); 7.2–7.4(m, 4H) | 39% Melting 131° C. Point |

-continued

| | | | |
|---|---|---|---|
| 35 | ![structure: (CH2)4OCH2C≡CCl with dioxane spiro, C(CH3)2] | 1.33(s, 3H); 1.38(s, 3H); 1.4–1.7 (m, 6H); 3.48(t, 2H); 3.9–4.1(m, 3H); 4.24(s, 2H) | 94% | structure:

R\   CH2—O—CH2—C≡CCl
 \ /
  C
 / \
O   O
 \ /
  C
 / \
CH3 CH3

| | | | |
|---|---|---|---|
| 36 | R = CH3 | 0.86(s, 3H); 1.37(s, 3H); 1.41 (s, 3H); 3.5–3.8(m, 6H); 4.28 (s, 2H) | 86% |
| 37 | R = C2H5 | 0.85(t, 3H); 1.36(q, 2H); 1.41 (s, 6H); 3.5–3.7(m, 6H); 4.3(s, 2H) | 90% Schmp. 65° C. |
| 37a | C2H5\  /CH2OCH2C≡CCl (1,3-dioxane with CH2) and C2H5\ /CH2OCH2C≡CCl (1,3-dioxolane isomer) | 0.83(t, 3H); 1.33(q, 2H); 3.44/3.81 (AB, 4H); 3.56 (s, 2H); 4.25(s, 2H); 4.62/4.87 (AB, 2H) | 75% Schmp. 45° C. | structure:

(CH2)K
 /   \
|     CH—CH2—O—CH2—C≡CCl
 \   /
   O

| | | | |
|---|---|---|---|
| 38 | K = 0 | 1.6–2.0(m, 4H); 3.4–4.1(m, 5H); 4.34(s, 2H) | 81% |
| 39 | K = 1 | 1.2–1.9(m, 6H); 3.4–4.0(m, 5H); 4.30(s, 2H) | 99% |
| 40 | ![tetrahydrofuran-OCH2C≡CCl] | 1.9–2.1(m, 2H); 3.7–3.9(m, 4H); 4.26(s, 2H); 4.29(m, 1H) | 78% |
| 41 | H5C2\  /CH2OCH2C≡CCl (oxetane) | 0.9(t, 3H); 1.75(q, 2H); 3.65 (s, 2H); 4.33(S, 2H); 4.3–4.5 (m, 4H) | 86% |
| 42 | CH3\  /CH2OCH2C≡CCl (oxetane) | 1.30(s, 3H); 3.55(s, 2H); 4.31(s, 2H); 4.33/4.48 (AB, 4H); | 85% |

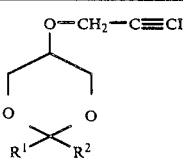

x mixture with the corresponding dioxane (if appropriate in each case cis/trans)

USE EXAMPLES 1-(Iodopropargyloxy)-propane-2,3-diol (DE-OS German Published Specification) No. 3,304,899) is used as the comparison substance.

EXAMPLE 1

To demonstrate the activity against fungi, the minimum inhibitory concentration (MIC) of active compounds according to the invention are determined:

Active compounds according to the invention are added in concentrations of 0.1 mg/l to 5,000 mg/l to an agar prepared from beer wort peptone. After solidification of the agar, contamination is effected with pure cultures of the test organisms listed in the table. After storage for 2 weeks at 28° C. and 60 to 70% relative atmospheric humidity, the MIC is determined. The MIC is the lowest concentration of active compound at which no growth at all of the species of microbe used takes place, and is given in the following table.

TABLE 1

| Test organism | Example No. 27 | 29 | 28 | 32 | 33 | 30 | 35 | 38 | 39 | 37 | 36 | 34 | 41 | Comparison |
|---|---|---|---|---|---|---|---|---|---|---|---|---|---|---|
| Penicillium glaucum | 15 | 15 | 15 | 10 | 20 | 50 | 50 | 5 | 5 | 100 | 50 | 10 | 5 | 50 |
| Chaetomium globosum | 10 | 3.5 | 10 | 10 | 7.5 | 3.5 | 7.5 | 10 | 5 | 15 | 20 | 3.5 | 5 | 100 |
| Aspergillus niger | 5 | 5 | 5 | 7.5 | 7.5 | 10 | 5 | 3.5 | 5 | 10 | 10 | 5 | 5 | 50 |
| Trichoderma viride | 100 | 200 | 100 | 50 | 100 | 750 | 500 | 75 | 50 | 500 | 200 | 1000 | 100 | 500 |
| Alternaria tenuis | 10 | 50 | 35 | 5 | 50 | 50 | 100 | 5 | 5 | 100 | 50 | 15 | 15 | 50 |
| Aureobasidium pullulans | 20 | 35 | 20 | 10 | 35 | 200 | 100 | 5 | 10 | 150 | 75 | 20 | 20 | 50 |
| Sclerophoma pityophila | 20 | 20 | 20 | 5 | 10 | 50 | 50 | 5 | 5 | 75 | 50 | 15 | 35 | 50 |
| Lentinus tigrinus | 10 | 20 | 20 | 75 | 10 | 50 | 50 | 10 | 5 | 100 | 10 | 1000 | 10 | 50 |

EXAMPLE 2

Action against bacteria

Active compounds according to the invention are added in concentrations of 1 to 5,000 ppm to an agar containing broth as the nutrient medium. Thereafter, the nutrient medium is infected in each case with the test organisms listed in Table II and the infected medium is kept at 28° C. and 60 to 70% relative atmospheric humidity for 2 weeks. The MIC is the lowest concentration of active compound at which no growth at all of the species of microbe used takes place. The MIC values are given in Table II.

TABLE II

MIC values in mg/l on action of the active compounds shown below on bacteria

| Test organism | Example No. 27 | 28 | 32 | 35 | 38 | 39 | 36 | 41 | Comparison |
|---|---|---|---|---|---|---|---|---|---|
| Escherichia coli | 500 | 500 | 200 | 750 | 200 | 500 | 750 | 500 | 200 |
| Staphylococcus aureus | 200 | 100 | 500 | 100 | 100 | 100 | 100 | 200 | 200 |

EXAMPLE 3

(Action against slime organisms)

Substances according to the invention are used in concentrations of in each case 0.1 to 100 mg/l in Allens nutrient solution (*Arch. Mikrobiol.*, 17, 34 to 53 (1952)), containing, in 4 liters of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam, dissolved in a little acetone. Shortly beforehand, the nutrient solution is infected with slime organisms (about $10^6$ germs/ml) which have been isolated from the spinning water circulations used in the preparation of polyamide. Nutrient solutions which contain the minimum inhibitory concentration (MIC) or larger concentrations of active compound are still completely clear after culture at room temperature for 3 weeks, that is to say the marked multiplication of the microbes and slime formation noticeable after 3 to 4 days in nutrient solutions containing no active compound are absent.

TABLE III

MIC values in mg/l on action of the substances shown below on slime organisms

| Active compound | MIC in mg/l |
|---|---|
| Examples 27 | 25 |
| 29 | 15 |
| 28 | 25 |
| 35 | 25 |
| 38 | 25 |
| 39 | 25 |
| 37 | 25 |
| 36 | 25 |
| Comparison | 35 |

EXAMPLE 4

A mixed culture of green, blue, brown and siliceous algae (*Stichococcus bacillaris* Naegeli, *Euglena gracilis* Klebs, *Chlorella pyrenoidosa* Chick, *Phormidium foveolarum* Gomont, *Oscillatoria geminata* Meneghini and *Phaeodactylum tricornutum* Bohlin) is added, while bubbling through air, to Allens nutrient solution (*Arch. Mikrobiol.*, 17, 34 to 53 (1952)), containing, in 4 liters of sterile water, 0.2 g of ammonium ammonium chloride, 4.0 g of sodium nitrate, 1.0 g of dipotassium hydrogen phosphate, 0.2 g of calcium chloride, 2.05 g of magnesium sulphate and 0.02 g of iron chloride. After 2 weeks, the nutrient solution is coloured deep green-blue by intensive algae growth. The destruction of the algae after addition of active compounds according to the invention is detected by decoloration of the nutrient solution.

TABLE IV

| Algae-destroying concentration (mg/l) of the substances shown below | |
|---|---|
| Active compound | Destroying concentration in mg/l |
| Example 38 | 100 |
| Example 39 | 100 |
| Example 27 | 100 |
| Comparison | >100 |

It will be appreciate that the instant specification and claims are set forth by way of illustration and not limitation, and that various modifications and changes may be made without departing from the spirit and scope of the present invention.

What is claimed is:

1. An iodopropargyl ether of the formula $$\begin{array}{c} R^1 \diagdown \diagup (CH_2)_n-O-CH_2-C\equiv CI \\ (CH_2)_m \quad (CH_2)_l \\ | \quad \quad | \\ (A)_k \quad \quad O \\ R^2 \diagdown \diagup R^3 \end{array}$$

wherein,
A is a methylene group or oxygen,
$R^1$ denotes hydrogen or lower alkyl,
$R^2$ and $R^3$ are identical or different and represent hydrogen, lower alkyl, alkenyl or unsubstituted or halogen-substituted phenyl, or together form a carbocyclic ring with 5 to 6 carbon atoms,
k is one, m is one or zero, l is one or zero, and
n is zero to four, with the proviso that the sum of m and l is one.

2. An iodopropargyl ether according to claim 1, wherein said lower alkyl is a straight-chain or branched alkyl with 1 to 6 carbon atoms.

3. An iodopropargyl ether according to claim 2, wherein said lower alkyl has 1 to 4 carbon atoms.

4. An iodopropargyl ether according to claim 1, wherein said halogen is chlorine.

5. An iodopropargyl ether according to claim 1, wherein
$R^1$ is hydrogen,
$R^2$ is hydrogen or lower alkyl,
$R^3$ is selected from the group consisting of hydrogen, lower alkyl, phenyl and chlorophenyl, and n is zero.

6. An iodopropargyl ether according to claim 1, wherein A is oxygen, l is zero, m is one and k is one.

7. An iodopropargyl ether according to claim 1, wherein A is oxygen, k is one, l is one and m is zero.

8. An iodopropargyl ether according to claim 1, wherein A is a methylene group, k is one, m is one or zero, l is one or zero, with the proviso that the sum of m and l is one.

9. An iodopropargyl ether according to claim 1, wherein A is a methylene group, k is one, m is one and l is zero.

10. A microbicidal composition comprising (a) a microbicidally effective amount of an iodopropargyl ether of the formula $$\begin{array}{c} R^1 \diagdown \diagup (CH_2)_n-O-CH_2-C\equiv CI. \\ (CH_2)_m \quad (CH_2)_l \\ | \quad \quad | \\ (A)_k \quad \quad O \\ R^2 \diagdown \diagup R^3 \end{array}$$

wherein
A represents oxygen or a methylene group,
$R^1$ denotes hydrogen or lower alkyl,
$R^2$ and $R^3$ are identical or different and represent hydrogen, lower alkyl, alkenyl or unsubstituted or halogen-substituted phenyl, or together form a carbocyclic ring with 5 to 6 carbon atoms,
l represents zero or one,
m represents zero or one,
k denotes one, and
n denotes an integer from zero to four, with the proviso that the sum of m and l is one, and (b) an extender selected from the group consisting of a liquid solvent, a solid carrier, a surface active agent and mixtures thereof.

11. A composition according to claim 10, wherein A is oxygen, k is one, l is one and m is zero.

12. A composition according to claim 10, wherein A is a methylene group, k is one, m is one and l is zero.

13. A composition according to claim 10, wherein A is oxygen, l is zero, m is one and k is one.

14. A composition according to claim 10, wherein the solvent is selected from the group consisting of water, alcohols, ketones and liquid hydrocarbons.

15. A composition according to claim 14, wherein the alcohol is selected from the group consisting of ethanol, isopropanol and benzyl alcohol, wherein the ketone is selected from the group consisting of acetone and methyl ethyl ketone.

16. A composition according to claim 10, wherein the solvent is selected from the group consisting of benzine and 1,2-dichloroethane.

* * * * *